US008071331B2

(12) United States Patent
Summer et al.

(10) Patent No.: US 8,071,331 B2
(45) Date of Patent: Dec. 6, 2011

(54) METHOD OF PRODUCING AMINO ACID METAL CHELATES

(75) Inventors: Paul Summer, Oskaloosa, IA (US); Shinya Tachibana, Oskaloosa, IA (US); Randall Vos, New Sharon, IA (US)

(73) Assignee: Ajinomoto U.S.A., Inc., Fort Lee, NJ (US)

( * ) Notice: Subject to any disclaimer, the term of this patent is extended or adjusted under 35 U.S.C. 154(b) by 0 days.

(21) Appl. No.: 12/477,300

(22) Filed: Jun. 3, 2009

(65) Prior Publication Data
US 2010/0035305 A1 Feb. 11, 2010

Related U.S. Application Data (60) Provisional application No. 61/058,348, filed on Jun. 3, 2008.

(51) Int. Cl.
- *C12P 21/06* (2006.01)
- *C12P 13/04* (2006.01)
- *C12P 13/08* (2006.01)
- *C12P 13/14* (2006.01)

(52) U.S. Cl. ....... 435/68.1; 435/106; 435/107; 435/108; 435/109; 435/110; 435/111; 435/112; 435/113; 435/114; 435/115

(58) Field of Classification Search ............. 435/68.1, 435/106, 107, 108, 109, 110, 111, 112, 113, 435/114, 115, 116
See application file for complete search history.

(56) References Cited

U.S. PATENT DOCUMENTS

| | | | |
|---|---|---|---|
| 3,969,540 A | 7/1976 | Jensen | |
| 4,473,589 A | 9/1984 | Freeman et al. | |
| 5,698,724 A | 12/1997 | Anderson et al. | |
| 6,323,354 B1 | 11/2001 | Moore | |
| 6,541,051 B2 | 4/2003 | Anderson et al. | |
| 7,569,558 B2* | 8/2009 | Gupta | 514/100 |
| 2003/0158171 A1* | 8/2003 | Ashmead et al. | 514/184 |

OTHER PUBLICATIONS

H. Tokuda et al, "Effects of electrical pre-treatment on the hydrolysis of agricultural wastes.", *J. Brew. Soc. Japan*, 2006, vol. 101, No. 10, pp. 769-775 (English abstract provided).
Kirk-Othmer, *Encyclopedia of Chemical Technology*, Fourth Ed., Wiley-Interscience, NY, 1995, vol. 16, pp. 68-87.
Kirk-Othmer, *Encyclopedia of Chemical Technology*, Fourth Ed., Wiley-Interscience, NY, 1995, vol. 16. pp. 700-746.
Kirk-Othmer, *Encyclopedia of Chemical Technology*, Fourth Ed., Wiley-Interscience, NY, 1993, vol. 18. pp. 887-905.
Kirk-Othmer, *Encyclopedia of Chemical Technology*, Fourth Ed., Wiley-Interscience, NY, 1998, vol. 25, pp. 664-712.
Kirk-Othmer, *Encyclopedia of Chemical Technology*, Fourth Ed., Wiley-Interscience, NY, 1995, vol. 15, pp. 159-177.

* cited by examiner

*Primary Examiner* — Herbert J Lilling
(74) *Attorney, Agent, or Firm* — Oblon, Spivak, McClelland, Maier & Neustadt, L.L.P.

(57) ABSTRACT

A method of producing amino acid metal chelates includes producing an amino acid ligand by enzymatically hydrolyzing bacterial cells, and reacting the amino acid ligand with a metal cation.

31 Claims, 2 Drawing Sheets

METHOD OF PRODUCING AMINO ACID METAL CHELATES

CROSS REFERENCE TO RELATED APPLICATIONS

This application claims priority to U.S. Provisional Patent Application No. 61/058,348, filed Jun. 3, 2008, the disclosure of which is incorporated herein by reference in its entirety.

BACKGROUND

The present invention relates to methods of producing amino acid metal chelates.

Divalent cation metals are known to form chelate complexes with alpha amino acids. These complexes may be obtained by reacting the cation metals with pure amino acids (e.g., single and specific amino acids, such as methionine) as ligands. Alternatively, these complexes may be obtained by reacting the cation metals with a hydrolysate of a particular protein source.

U.S. Pat. No. 5,698,724 describes a method of preparing metal amino acid complexes in which amino acids are obtained by hydrolyzing protein of vegetable or animal origin. The protein is hydrolyzed with an acid, such as hydrochloric acid, and the resulting hydrolysate is reacted with a metal species, such as zinc oxide, to obtain the amino acid complexes.

U.S. Pat. No. 6,541,051 describes a method of preparing metal amino acid complexes in which amino acids are obtained by hydrolyzing soy protein. The protein is hydrolyzed with an acid, such as hydrochloric acid, and the resulting hydrolysate is reacted with a metal species, such as zinc oxide, to obtain the amino acid complexes.

Performing acid hydrolysis of feed proteins to obtain amino acid ligands is asserted to provide an economic advantage over using pure amino acids as ligands. However, performing acid hydrolysis can be disadvantageous because the use of strong mineral acids requires special equipment and safety precautions. In addition, the dissociated anion from the strong mineral acid (e.g., sulfate or chloride) is likely to remain in the hydrolysate and dilute the amino acid metal chelate that is sought to be obtained. Efforts to remove such anions from the hydrolysate are likely to increase costs, and the by-product salt containing the anion must be disposed of in some manner. Moreover, to obtain complete hydrolysis by acid hydrolysis requires expensive high pressure tanks as well as a high input of energy as heat and pressure.

U.S. Pat. No. 6,323,354 describes a method of preparing amino acid transition metal chelates from lipoproteins and transition metal salts. Amino acids are obtained by hydrolyzing lipoproteins obtained from, e.g., fractured cell walls from microbes generated in the biological synthesis of amino acids. The lipoproteins are hydrolyzed with a strong base, such as sodium hydroxide, and the resulting hydrolysate is reacted with a metal species, such as zinc sulfate, to obtain the amino acid transition metal chelates.

Employing base hydrolysis to obtain amino acid metal chelates poses similar problems to those described above with respect to acid hydrolysis. In addition, base hydrolysis may convert amino acids from L-isomers to D-isomers, making them nutritionally unavailable for protein production.

It is known to employ enzyme hydrolysis in various particular contexts. For example, it is known to hydrolyze starch using amylitic enzymes, to hydrolyze cellulose using cellulase and to hydrolyze proteins using proteinases. As evidenced by the absence of a commercially-used process employing such means, enzyme hydrolysis is not known to be particularly effective in preparing amino acid or short peptide ligands for use in producing amino acid metal chelates.

U.S. Pat. No. 3,969,540 describes a method of preparing metal proteinates from protein hydrolysates and metal salts. Protein hydrolysates are obtained by enzymatically hydrolyzing sources of protein such as yeast. The sources of protein are hydrolyzed using proteases. Yeast is believed to be an unacceptable source of protein for use in enzymatic hydrolysis to form amino acid ligands for chelating with metals (e.g., for use in feedstuffs) because yeast has a relatively low protein content and high purine content.

SUMMARY

In view of the foregoing, it is an object of the present invention to provide a method of producing amino acid metal chelates, wherein an amino acid and/or a short peptide ligand is obtained without using harsh chemicals that have no nutritive value in the final product by employing enzyme hydrolysis followed by chelation with a metal cation.

It is a further object of the present invention to provide a method of producing amino acid metal chelates, wherein chelates with high metal concentration (and low concentration of contaminating ions) can be economically obtained.

It is a further object of the present invention to provide a method of producing amino acid metal chelates, wherein a specialized proteinacious feedstock, bacterial cell bodies, is used as an economical source of crude protein.

In various exemplary embodiments, methods of producing amino acid metal chelates according to the present invention include producing an amino acid ligand by enzymatically hydrolyzing bacterial cells, and reacting the amino acid ligand with a metal cation.

In various exemplary embodiments, processes for making foliar fertilizers according to the present invention include producing amino acid metal chelates as described herein, and processing the amino acid metal chelates into a form suitable for application to crops.

In various exemplary embodiments, foliar fertilizers according to the present invention include foliar fertilizers obtained by the methods described herein.

In various exemplary embodiments, processes of making agricultural products according to the present invention include preparing foliar fertilizers by the methods described herein, applying the foliar fertilizers to crops, and harvesting the crops to obtain the agricultural products.

In various exemplary embodiments, processes of making agricultural products according to the present invention include applying foliar fertilizers as described herein to crops, and harvesting the crops to obtain the agricultural products.

In various exemplary embodiments, processes of making consumer products according to the present invention include preparing foliar fertilizers by the methods described herein, applying the foliar fertilizers to crops, harvesting the crops to obtain agricultural products, and processing the agricultural products to obtain the consumer products.

In various exemplary embodiments, processes of making consumer products according to the present invention include applying foliar fertilizers as described herein to crops, harvesting the crops to obtain agricultural products, and processing the agricultural products to obtain the consumer products.

In various exemplary embodiments, processes of making industrial products according to the present invention include preparing foliar fertilizers by the methods described herein, applying the foliar fertilizers to crops, harvesting the crops to obtain agricultural products, and processing the agricultural products to obtain the industrial products.

In various exemplary embodiments, processes of making industrial products according to the present invention include applying foliar fertilizers as described herein to crops, harvesting the crops to obtain agricultural products, and processing the agricultural products to obtain the industrial products.

In various exemplary embodiments, processes for making soil adjuvants according to the present invention include producing amino acid metal chelates as described herein, and processing the amino acid metal chelates into a form suitable for application to crops.

In various exemplary embodiments, soil adjuvants according to the present invention include soil adjuvants obtained by the methods described herein.

In various exemplary embodiments, processes of making agricultural products according to the present invention include preparing soil adjuvants by the methods described herein, applying the soil adjuvants to crops, and harvesting the crops to obtain the agricultural products.

In various exemplary embodiments, processes of making agricultural products according to the present invention include applying soil adjuvants as described herein to crops, and harvesting the crops to obtain the agricultural products.

In various exemplary embodiments, processes of making consumer products according to the present invention include preparing soil adjuvants by the methods described herein, applying the soil adjuvants to crops, harvesting the crops to obtain agricultural products, and processing the agricultural products to obtain the consumer products.

In various exemplary embodiments, processes of making consumer products according to the present invention include applying soil adjuvants as described herein to crops, harvesting the crops to obtain agricultural products, and processing the agricultural products to obtain the consumer products.

In various exemplary embodiments, processes of making industrial products according to the present invention include preparing soil adjuvants by the methods described herein, applying the soil adjuvants to crops, harvesting the crops to obtain agricultural products, and processing the agricultural products to obtain the industrial products.

In various exemplary embodiments, processes of making industrial products according to the present invention include applying soil adjuvants as described herein to crops, harvesting the crops to obtain agricultural products, and processing the agricultural products to obtain the industrial products.

In various exemplary embodiments, processes of making feedstuffs according to the present invention include producing amino acid metal chelates by the methods described herein, and incorporating the amino acid metal chelates into a feedstuff composition.

In various exemplary embodiments, feedstuffs according to the present invention include feedstuffs obtained by the methods described herein.

In various exemplary embodiments, processes for raising livestock, according to the present invention include making a feedstuff by the processes described herein, and feeding livestock the feedstuff.

In various exemplary embodiments, processes for raising livestock according to the present invention include feeding livestock the feedstuffs described herein.

In various exemplary embodiments, processes for making meat according to the present invention include making a feedstuff by methods described herein, feeding livestock the feedstuff, and harvesting meat from the livestock.

In various exemplary embodiments, processes for making meat according to the present invention include feeding livestock the feedstuffs described herein, and harvesting meat from the livestock.

In various exemplary embodiments, processes for making milk according to the present invention include making a feedstuff by the methods described herein, feeding livestock the feedstuff, and harvesting milk from the livestock.

In various exemplary embodiments, processes for making milk according to the present invention include feeding livestock the feedstuffs described herein, and harvesting milk from the livestock.

In various exemplary embodiments, processes for making a dairy product according to the present invention include making a feedstuff by the methods described herein, feeding livestock the feedstuff, harvesting milk from the livestock, and converting the milk into the dairy product.

In various exemplary embodiments, processes for making a dairy product according to the present invention include feeding livestock the feedstuffs described herein, harvesting milk from the livestock, and converting the milk into the dairy product.

In various exemplary embodiments, processes for making eggs or an egg product according to the present invention include making a feedstuff by the methods described herein, feeding livestock the feedstuff, and harvesting eggs from the livestock.

In various exemplary embodiments, processes for making eggs or an egg product according to the present invention include feeding livestock the feedstuffs described herein, and harvesting eggs from the livestock.

In various exemplary embodiments, processes for making wool according to the present invention include making a feedstuff by the methods described herein, feeding livestock the feedstuff, and harvesting wool from the livestock.

In various exemplary embodiments, processes for making wool according to the present invention include feeding livestock the feedstuffs described herein, and harvesting wool from the livestock.

In various exemplary embodiments, processes for making fur according to the present invention include making a feedstuff by the methods described herein, feeding livestock the feedstuff, and harvesting fur from the livestock.

In various exemplary embodiments, processes for making fur according to the present invention include feeding livestock the feedstuffs described herein, and harvesting fur from the livestock.

In various exemplary embodiments, processes for making leather according to the present invention include making a feedstuff by the methods described herein, feeding livestock the feedstuff, harvesting skin from the livestock, and converting the skin into the leather.

In various exemplary embodiments, processes for making leather according to the present invention include feeding livestock the feedstuffs described herein, harvesting skin from the livestock, and converting the skin into the leather.

In various exemplary embodiments, processes of making a pet food according to the present invention include producing amino acid metal chelates by the methods described herein, and incorporating the amino acid metal chelates into a pet food composition.

In various exemplary embodiments, pet foods according to the present invention include pet foods obtained by the processes described herein.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF EXEMPLARY EMBODIMENTS

In various exemplary embodiments of the present invention, methods of producing amino acid metal chelates include producing an amino acid ligand by enzymatically hydrolyzing bacterial cells, and reacting the amino acid ligand with a metal cation. Producing the amino acid metal chelates can include producing metal chelates of at least one of free amino acids, dipeptides and tripeptides.

As discussed above, various exemplary embodiments of the methods according to the present invention include producing an amino acid ligand by enzymatically hydrolyzing bacterial cells. Methods according to the present invention are both feasible and advantageous because they rely on the use of protein sources of amino acids that are amenable to enzymatic hydrolysis, such as bacterial cells. By employing such protein sources of amino acids, the negative effects of performing strong acid or base hydrolysis, as employed in known methods, can be avoided and economical, highly-concentrated amino acid metal chelates can be obtained.

Various sources of bacterial cells are feasibly employed in the methods according to the present invention. For example, bacterial cells can be obtained from any industrial process that generates bacterial mass such as ethanol production, organic acid production, and waste-water treatment. In exemplary embodiments, the bacterial cells used to produce amino acid metal chelates are gram negative. As indicated above, a particularly preferred source of bacterial cells are bacterial cells obtained as a by-product of amino acid production. Bacterial cells may be provided in spent media from production of one or more amino acids including, but not limited to, arginine, histidine, isoleucine, leucine, lysine, methionine, phenylalanine, threonine, tryptophan, valine, glycine, serine, cysteine, tyrosine, alanine, aspartic acid, glutamic acid, proline, asparagines and glutamine. Desirably, bacterial cells are provided in spent media from production of one or more amino acids including, but not limited to, lysine, threonine, tryptophan and glutamic acid. In a particularly preferred embodiment, the bacterial cells used to produce amino acid metal chelates are bacterial cells present in spent media obtained from production of lysine.

Plant-, animal- and fungal-derived proteins, such as soybean protein, meat meal and yeast protein, are not believed to be effective sources of protein for enzymatic hydrolysis. Plant-derived proteins have more complex tertiary and quaternary structures than bacterial proteins and are believed to be more resistant to enzymatic hydrolysis. Animal-derived proteins are naturally resistant to hydrolysis and believed to be the most difficult to break down. Organisms, such as yeast, are believed to have a lower protein content than bacteria, and proteins, such as yeast proteins, are believed to have a higher purine content than bacterial proteins—excessive purine intake can lead to gout in some animals. For at least the foregoing reasons, bacterial cells are used in embodiments of the present invention. However, the present application is intended to encompass embodiments where plant-, animal- and fungal-derived proteins are employed, in lieu of or in addition to bacterial-derived proteins, as appropriate.

In various exemplary embodiments, the bacterial cells used to produce amino acid metal chelates are provided in the form of a cell cream (e.g., a cell cream obtained as a by-product of lysine production). The cell cream may have a solids content of from 1 to 30 weight percent or from about 1 to about 30 weight percent. In some embodiments, the cell cream may have a solids content of from 5 to 25 weight percent or from about 5 to about 25 weight percent. In further embodiments, the cell cream may have a solids content of from 10 to 20 weight percent or from about 10 to about 20 weight percent.

In embodiments, the bacterial cells used to produce amino acid metal chelates are provided in the form of a cell cream having a nitrogen content of from 0.12 to 4 weight percent or from about 0.12 to about 4 weight percent. In further embodiments, the cell cream may have a nitrogen content of from 0.63 to 3.2 weight percent or from about 0.63 to about 3.2 weight percent. In still further embodiments, the cell cream may have a nitrogen content of from 1.2 to 2.4 weight percent or from about 1.2 to about 2.4 weight percent.

In various exemplary embodiments of the methods of the present invention, enzymatic hydrolysis of bacterial cells may be carried out using any suitable enzyme or enzymatic composition. The enzyme source may be any enzyme or mixture of enzymes that is capable of hydrolyzing proteins of the bacterial cells into free amino acids and/or short peptides. The bacterial cells may be hydrolyzed with a purified enzyme. The bacterial cells may also be hydrolyzed with a mixture of an enzyme and a medium in which the enzyme was prepared. In embodiments, the bacterial cells may be hydrolyzed with an enzyme of plant origin. In other embodiments, the bacterial cells may be hydrolyzed with an enzyme of animal origin. In further embodiments, the bacterial cells may be hydrolyzed with an enzyme of bacterial origin. In still embodiments, the bacterial cells may be hydrolyzed with an enzyme of fungal origin. In alternative embodiments, the bacterial cells may be hydrolyzed with a mixture of one or more enzymes of plant origin, enzymes of animal origin, enzymes of bacterial origin, and enzymes of fungal origin. In exemplary embodiments, bacterial cells may be hydrolyzed with one or more of proteases, lipases and amylases. In some such embodiments, bacterial cells may be hydrolyzed with one or more of papain, bromelain, bacterial protease, fungal protease, trypsin, chymotrypsin, pepsin and rennin. In a particularly preferred embodiment, bacterial cells are hydrolyzed with pancreatin. As would be well-understood by one of ordinary skill in the art, pancreatin includes a mixture of digestive enzymes, proteases, lipases and amylases.

As discussed above, in various exemplary embodiments of the present invention, methods of producing amino acid metal chelates include producing amino acid ligands by enzymatically hydrolyzing bacterial cells obtained as a by-product of amino acid production. Enzymatically hydrolyzing bacterial cells may include combining an enzyme and bacterial cells in any suitable amount under any suitable conditions. Generally, quantities of reactants, reaction conditions, and sequences of reaction steps are selected to achieve ideal enzyme activity. In embodiments, enzymatically hydrolyzing bacterial cells may include combining an enzyme and bacterial cells in a weight ratio of from 0.1 to 10 g of enzyme per 100 g of nitrogen content of bacterial cells or from about 0.1 to about 10 g of enzyme per 100 g of nitrogen content of bacterial cells. In further embodiments, enzymatically hydrolyzing bacterial cells may include combining an enzyme and bacterial cells or from 0.5 to 7.5 g of enzyme per 100 g of nitrogen content of bacterial cells or from about 0.5 to about 7.5 g of enzyme per 100 g of nitrogen content of bacterial cells. In still further embodiments, enzymatically hydrolyzing bacterial cells may include combining an enzyme and bacterial cells in a weight ratio of from 1.0 to 5.0 g of enzyme per 100 g of nitrogen content of bacterial cells or from about 1.0 to about 5.0 g of enzyme per 100 g of nitrogen content of bacterial cells.

As indicated above, hydrolysis may be carried out under any suitable conditions. In various exemplary embodiments, hydrolysis may be carried out at a pH of from 2 to 10 or a pH of from about 2 to about 10. In further embodiments, hydrolysis may be carried out at a pH of from 4 to 8 or a pH of from about 4 to about 8. In still further embodiments, hydrolysis may be carried out at a pH of from 5.5 to 7 or a pH of from about 5.5 to about 7. It should be appreciated that each type of enzyme hydrolyzes at its own optimum pH optimum, and the optimum pH may vary depending on the rate and extent of hydrolysis desired. In various exemplary embodiments, hydrolysis may be carried out at a temperature of from 15.5° C. to 55° C. or a temperature of from about 15.5° C. to about 55° C. In further embodiments, hydrolysis may be carried out at a temperature of from 20° C. to 45° C. or a temperature of from about 20° C. to about 45° C. In still further embodiments, hydrolysis may be carried out at a temperature of from 27° C. to 39° C. or a temperature of from about 27° C. to about 39° C. In various exemplary embodiments, hydrolysis may be carried out for a period of from 2 hours to 120 hours or a period of from about 2 hours to about 120 hours. In further embodiments, hydrolysis may be carried out for a period of from 12 hours to 96 hours or a period of from about 12 hours to about 96 hours. In still further embodiments, hydrolysis may be carried out for a period of from 24 hours to 48 hours or a period of from about 24 hours to about 48 hours.

In various exemplary embodiments, any suitable method may be employed to improve the efficiency of the enzymatic hydrolysis of the bacterial cells. For example, enzymatically hydrolyzing bacterial cells may include combining an enzyme and the bacterial cells and agitating the combined enzyme and bacterial cells. Agitation may be performed by any suitable method. In exemplary embodiments, enzymatically hydrolyzing bacterial cells may include reacting an enzyme and the bacterial cells in the presence of a catalyst. Any catalyst that improves the efficiency of the enzyme or enzymes may be employed. Catalysts that may be employed include heterogeneous catalysts, homogeneous catalysts and/or electrocatalysts. In some such embodiments, the catalyst may include iron. Other exemplary catalysts include copper, cobalt, nickel, boron, magnesium, calcium and rare earth metals, such as lanthium. Alternatively, enzymatically hydrolyzing bacterial cells may include reacting an enzyme and the bacterial cells while electric current is applied.

As discussed above, in various exemplary embodiments of the present invention, methods of producing amino acid metal chelates include reacting amino acid ligands obtained by enzymatically hydrolyzing bacterial cells with metal cations. That is, after hydrolysis of the bacterial cells is carried out, metal cations are added to the hydrolysate to form organic complexes with the obtained free amino acids and small peptides. The hydrolysate and metal cations are mixed in amounts and under conditions suitable to adequately dissolve the metal cations and allow for chelation of the metal cations with free amino acids and small peptides obtained from the bacterial cells.

As indicated above, amino acid ligands may be reacted with metal cations under any suitable conditions. In various exemplary embodiments, amino acid ligands may be employed in an amount of 1 mole amino acid ligand N to 4 moles amino acid ligand N per mole of metal or in an amount of about 1 mole amino acid ligand N to about 4 moles amino acid ligand N per mole of metal. In further embodiments, amino acid ligands may be employed in an amount of 2 moles amino acid ligand N to 3 moles amino acid ligand N per mole of metal or in an amount of about 2 mole amino acid ligand N to about 3 moles amino acid ligand N per mole of metal. An ideal pH for a reaction between amino acid ligands and metal cations is a pH above the isoelectric point of the respective amino acid ligands. For amino acids with neutral side chains the isoelectric point is no less than about pH 6.3. Three protein amino acids have high isoelectric points—the amino acids with basic side chains: lysine, arginine and histidine having pHs of 9.7, 10.7 and 7.6, respectively. Accordingly, in various exemplary embodiments, amino acid ligands and metal cations are reacted at a pH of from 5 to 11 or a pH of from about 5 to about 11. In further embodiments, amino acid ligands and metal cations are reacted at a pH of from 6 to 8 or a pH of from about 6 to about 8. In still further embodiments, amino acid ligands and metal cations are reacted at a pH of from 6.5 to 8 or a pH of from about 6.5 to about 8. In various exemplary embodiments, amino acid ligands and metal cations are reacted at a temperature of from 20° C. to 80° C. or from about 20° C. to about 80° C. In further embodiments, amino acid ligands and metal cations are reacted at a temperature of from 25° C. to 60° C. or from about 25° C. to about 60° C. In still further embodiments, amino acid ligands and metal cations are reacted at a temperature of from 30° C. to 50° C. or from about 30° C. to about 50° C.

In embodiments, amino acid ligands are reacted with metal cations having a valence of two or more. In some such embodiments, the metal cations may include one or more of calcium, magnesium, chromium, manganese, iron, copper, cobalt, boron, molybdenum, vanadium and zinc. Metal cations that may be reacted with amino acid ligands may be provided in the form of salts of metal cations. In some such cases, the salts may be chlorides or sulfates. Alternatively, metal cations that may be reacted with amino acid ligands may be provided in the form of oxides or hydroxides of metal cations. In various exemplary embodiments, metal cations may be provided in the form of one or more of copper sulfate, cobalt oxide, cobalt chloride, zinc oxide, zinc sulfate, magnesium oxide, magnesium chloride and magnesium sulfate.

Various exemplary embodiments of the methods of present invention may further include a pretreatment before enzymatically hydrolyzing bacterial cells. The efficiency of bacterial protein hydrolysis using enzymes can be improved by using various pre-treatment methods. Such pretreatment methods are believed to degrade the structure of the bacterial cells and, thus, increase the rate and extent of hydrolysis by an enzyme. By increasing the efficiency of bacterial protein hydrolysis, it is possible to perform hydrolysis using less enzyme or perform hydrolysis in less time that would ordinarily be required with a given amount of enzyme. It is particularly desirable to perform hydrolysis using less enzyme, as a reduction in the amount of enzyme used can substantially reduce production costs.

In embodiments, the bacterial cells are treated with electrical current before enzymatically hydrolyzing the cells. In further embodiments, the bacterial cells are treated with a mild acid before enzymatically hydrolyzing the cells. The bacterial cells may also be treated with a mild alkali before enzymatically hydrolyzing the cells. The bacterial cells may be treated with ultrasonic vibration before enzymatically hydrolyzing the cells. The bacterial cells may be treated with supercritical water before enzymatically hydrolyzing the cells. Further, the bacterial cells may be treated with supercritical carbon dioxide before enzymatically hydrolyzing the bacterial cells.

Electrical current may be applied to bacterial cells by any suitable means and under any suitable conditions. Exemplary means and conditions for applying electrical current are described, for example, in Tokuda, et al., "Effects of electrical pre-treatment on the hydrolysis of agricultural wastes," J. Brewing Soc. Jap., 101(10): 769-775 (2006), which is incorporated herein by reference in its entirety. In various exemplary embodiments, electrical current is applied in an amount of from 2 to 120 V or from about 2 to about 120 V. In further embodiments, electrical current is applied in an amount of from 5 to 80 V or from about 5 to about 80 V. In still further embodiments, electrical current is applied in an amount of from 10 to 40 V or from about 10 to about 40 V. In various exemplary embodiments, electrical current is applied for a period of from 1 to 60 minutes or from about 1 to about 60 minutes. In further embodiments, electrical current is applied for a period of from 2 to 20 minutes or from about 2 to about 20 minutes. In still further embodiments, electrical current is applied for a period of from 4 to 10 minutes or from about 4 to about 10 minutes. In various exemplary embodiments, metal cations (e.g., the metal cations to be chelated) are added to the bacterial cells (e.g., including medium—cell cream) before applying electrical current, to increase the conductivity of bacterial cells and enhance the effectiveness pretreatment.

In various exemplary embodiments, a mild acidic pretreatment is carried about by adjusting a pH of the bacterial cells. In embodiments, pH is adjusted using an acid such as hydrochloric acid or sulfuric acid. In embodiments, the pH is adjusted to from 3 to 5 or from about 3 to about 5. In further embodiments, the pH is adjusted to from 3.5 to 4.5 or from about 3.5 to about 4.5. In embodiments, mild acidic pretreatment may be carried out at a temperature of from 100° C. to 130° C. or from about 100° C. to about 130° C. In various exemplary embodiments, mild acidic pretreatment may be carried out for a period of from 0.25 hours to 10 hours or from about 0.25 hours to about 10 hours. In further embodiments, mild acidic pretreatment may be carried out for a period of from 0.5 hours to 5 hours or from about 0.5 hours to about 5 hours. In still further embodiments, mild acidic pretreatment may be carried out for a period of from 1 hour to 3 hours or from about 1 hour to about 3 hours.

In various exemplary embodiments, a mild basic pretreatment is carried about by adjusting a pH of the bacterial cells. In embodiments, pH is adjusted using a base such as sodium hydroxide, potassium hydroxide or ammonia. In embodiments, the pH is adjusted to from 9 to 12 or from about 9 to about 12. In further embodiments, the pH is adjusted to from 10 to 11 or from about 10 to about 11. In embodiments, mild basic pretreatment may be carried out at a temperature of from 100° C. to 130° C. or from about 100° C. to about 130° C. In various exemplary embodiments, mild basic pretreatment may be carried out for a period of from 0.25 hours to 10 hours or from about 0.25 hours to about 10 hours. In further embodiments, mild basic pretreatment may be carried out for a period of from 0.5 hours to 5 hours or from about 0.5 hours to about 5 hours. In still further embodiments, mild basic pretreatment may be carried out for a period of from 1 hour to 3 hours or from about 1 hour to about 3 hours.

As discussed above, methods according to the present invention may be carried out by first hydrolyzing bacterial cells to obtain amino acid ligands and then reacting the amino acid ligands with metal cations to obtain amino acid metal chelates. However, it should be appreciated that methods according to the present invention may be carried out in any suitable sequence. For example, in various exemplary embodiments of the methods of the present invention, the amino acid ligands may be produced and reacted with the metal cations simultaneously. In some such embodiments, bacterial cells, an enzyme and the metal cations are combined together in a single reaction vessel—that is, the metal to be chelated is admixed with the bacterial cells and enzyme before hydrolysis begins. As suggested above, proceeding in this manner allows hydrolysis and chelation occur simultaneously. Simultaneous hydrolysis and chelation may provide several advantages. For example, if amino acids or short peptides are immediately chelated with metal cations after being released from the bacterial cells, such amino acids and short peptides may be protected from degradation by contaminants. Bacterial contaminants can decarboxylate amino acids to produce biogenic amines such as histamine and cadaverine from histidine and lysine, respectively. Contaminants may also metabolize the carbon skeletons of amino acids. Such degradation will prevent the amino acids from forming chelate complexes with metal cations. In addition, the presence of metals in a reaction medium during hydrolysis may have an antibiotic effect, preventing microbial growth in the media. Copper may be particularly advantageous in this regard.

The present invention is directed to processes for making foliar fertilizers. In various exemplary embodiments, processes for making a foliar fertilizer may include producing amino acid metal chelates by the methods described above, and processing the amino acid metal chelates into a form suitable for application to crops. The present invention is further directed to foliar fertilizers obtained by such processes.

The present invention is further directed to processes of making agricultural products. In various exemplary embodiments, such processes include preparing foliar fertilizers by the methods described above, applying the foliar fertilizers to crops, and harvesting the crops to obtain agricultural products. Exemplary crops may include food crops and ornamental crops. Exemplary food crops may include fruits, vegetables and grains. Exemplary ornamental crops may include turfgrass, trees, shrubs and flowers. In further exemplary embodiments, such processes may include applying an already prepared foliar fertilizer to crops, and harvesting the crops to obtain agricultural products.

The present invention is further directed to processes of making consumer products. In various exemplary embodiments, such processes include preparing foliar fertilizers by the methods described above, applying the foliar fertilizers to crops as described above, harvesting the crops to obtain agricultural products, and processing the agricultural products to obtain consumer products. In further exemplary embodiments, such processes may include applying an already prepared foliar fertilizer to crops, harvesting the crops to obtain agricultural products, and processing the agricultural products to obtain consumer products.

The present invention is further directed to processes of making industrial products. In various exemplary embodiments, such processes include preparing foliar fertilizers by the methods described above, applying the foliar fertilizers to crops as described above, harvesting the crops to obtain agricultural products, and processing the agricultural products to obtain industrial products. In further exemplary embodiments, such processes may include applying an already prepared foliar fertilizer to crops, harvesting the crops to obtain agricultural products, and processing the agricultural products to obtain industrial products.

The present invention is directed to processes for making soil adjuvants. In various exemplary embodiments, processes for making a soil adjuvant may include producing amino acid metal chelates by the methods described above, and processing the amino acid metal chelates into a form suitable for application to crops. The present invention is further directed to soil adjuvants obtained by such processes.

The present invention is further directed to processes of making agricultural products. In various exemplary embodiments, such processes include preparing soil adjuvants by the methods described above, applying the soil adjuvants to crops (e.g., in wet or dry form), and harvesting the crops to obtain agricultural products. Exemplary crops may include food crops and ornamental crops. Exemplary food crops may include fruits, vegetables and grains. Exemplary ornamental crops may include turfgrass, trees, shrubs and flowers. In further exemplary embodiments, such processes may include applying an already prepared soil adjuvant to crops, and harvesting the crops to obtain agricultural products.

The present invention is further directed to processes of making consumer products. In various exemplary embodiments, such processes include preparing soil adjuvants by the methods described above, applying the soil adjuvants to crops as described above, harvesting the crops to obtain agricultural products, and processing the agricultural products to obtain consumer products. In further exemplary embodiments, such processes may include applying an already prepared soil adjuvant to crops, harvesting the crops to obtain agricultural products, and processing the agricultural products to obtain consumer products.

The present invention is further directed to processes of making industrial products. In various exemplary embodiments, such processes include preparing soil adjuvants by the methods described above, applying the soil adjuvants to crops as described above, harvesting the crops to obtain agricultural products, and processing the agricultural products to obtain industrial products. In further exemplary embodiments, such processes may include applying an already prepared soil adjuvant to crops, harvesting the crops to obtain agricultural products, and processing the agricultural products to obtain industrial products.

The present invention is directed to processes for making feedstuffs. Amino acid metal chelates may be particularly useful in providing mineral content to feedstuffs. In various exemplary embodiments, processes for making a feedstuff may include producing amino acid metal chelates by the methods described above, and incorporating the amino acid metal chelates into a feedstuff composition. The present invention is further directed to feedstuffs obtained by such processes.

In embodiments, the present invention provides novel processes for raising livestock by feeding livestock such a feedstuff. Such livestock includes cattle, oxen, bison, deer, pigs, goats, sheep, lambs, rabbits, lama, alpaca, foxes, mink, ermine, weasel, stoat, chinchilla, beavers, sables, otters, kangaroos, yaks, and fowl or poultry (including chickens, turkeys, ducks, game hens, ostrich, emu, and pheasants) and fish (including salmon, catfish, etc) and reptiles (including alligators, crocodiles, lizards, snakes, etc.). In exemplary embodiments, livestock includes ruminant animals.

These livestock may be fed the feedstuff of the present invention at any time and in any amount during their life. That is, the livestock may be fed the feedstuff of the present invention either by itself or as part of a diet which includes other feedstuffs. Moreover, the livestock may be fed the feedstuff of the present invention at any time during their lifetime. The livestock may be fed the feedstuff of the present invention continuously, at regular intervals, or intermittently. The livestock may be fed the feedstuff of the present invention in an amount such that it accounts for all, a majority, or a minority of the protein in the livestock's diet for any portion of time in the animal's life. Preferably, the livestock is fed the feedstock of the present invention in an amount such that it accounts for a majority of the protein in the animal's diet for a significant portion of the animal's lifetime.

In another embodiment, the present invention provides novel processes for making meat by harvesting meat from livestock which have been fed such a feedstuff. The livestock in this embodiment are the same as those described above in connection with the present process for raising livestock. The feeding may be carried out as described above in connection with the process for raising livestock.

The meat may be harvested at any suitable time during the animal's lifetime. The harvesting of the meat may be carried out using the techniques conventional in the art of butchering. Typical meats to be harvested include, beef, pork, mutton, lamb, venison, bison, rabbit, chicken, turkey, duck, ostrich, emu, pheasant, etc. The meat may be sold fresh or frozen. The meat may be processed as described in Kirk-Othmer, *Encyclopedia of Chemical Technology*, Fourth Ed., Wiley-Interscience, NY, vol. 16, pp. 68-87, 1995, which is incorporated herein by reference.

In another embodiment, the present invention provides novel processes for making milk by harvesting milk from livestock which have been fed such a feedstuff. The livestock in this embodiment are those which produce milk, such as cattle, oxen, bison, deer, pigs, goats, sheep, etc. The feeding may be carried out as described above in connection with the process for raising livestock. The harvesting of the milk may be carried out using the conventional techniques known to those in the art. The milk may be processed, stored, cooled, shipped, and packaged, as described in Kirk-Othmer, *Encyclopedia of Chemical Technology*, Fourth Ed., Wiley-Interscience, NY, vol. 16, pp. 700-746, 1995, which is incorporated herein by reference.

In another embodiment, the present invention provides processes for making a dairy product from the milk harvested from an animal which has been fed the feedstuff of the present invention. Such dairy products include evaporated and condensed milk, dry milk, cream, anhydrous milk fat, butter, buttermilk, cheese, yogurt, and frozen desserts (such as ice cream, frozen yogurt, ice milk, sherbets, and mellorine), lactose, and casein. The conversion of the milk into the dairy product may be carried out using conventional techniques known to those skilled in the art as described in Kirk-Othmer, *Encyclopedia of Chemical Technology*, Fourth Ed., Wiley-Interscience, NY, vol. 16, pp. 700-746, 1995, which is incorporated herein by reference.

In another embodiment, the present invention provides novel processes for making eggs or an egg product by harvesting eggs from livestock which have been fed such a feedstuff. The livestock in this embodiment are those which produce eggs, such as chickens, turkeys, ducks, game hens, ostrich, emu, pheasants, etc. The feeding may be carried out as described above in connection with the process for raising livestock. The egg products include liquid egg products (such as egg white, egg yolk, whole egg, extended shelf life refrigerated liquid egg products, and concentrated sugared whole egg), frozen egg products (such as egg white, plain whole egg, whole egg with yolk added, plain egg yolk, fortified whole egg with corn syrup, sugared egg yolk, salted egg yolk, salted whole egg, and scrambled eggs and omelets), and dried egg products (such as dried egg white, dried whole egg, and dried egg yolk). The production of the eggs and the egg products may be carried out using the conventional techniques known to those in the art as described in Kirk-Othmer, *Encyclopedia of Chemical Technology*, Fourth Ed., Wiley-Interscience, NY, vol. 18, pp. 887-905, 1993, which is incorporated herein by reference.

In another embodiment, the present invention provides novel processes for making wool by harvesting wool from livestock which have been fed such a feedstuff. The livestock in this embodiment are those which produce wool, such as goats, sheep, lambs, lama, alpaca, etc. The feeding may be carried out as described above in connection with the process for raising livestock. The wool may be harvested and treated by conventional techniques known to those skill in the art and as described in Kirk-Othmer, *Encyclopedia of Chemical Technology*, Fourth Ed., Wiley-Interscience, NY, vol. 25, pp. 664-712, 1998, which is incorporated herein by reference.

In another embodiment, the present invention provides novel processes for making fur by harvesting fur from livestock which have been fed such a feedstuff. The livestock in this embodiment are those which produce fur, such as rabbits, lama, alpaca, foxes, mink, ermine, weasel, stoat, chinchilla, beavers, sables, otters, etc. The feeding may be carried out as described above in connection with the process for raising livestock. The fur may be harvested and treated by conventional techniques known to those skill in the art and as described in Kirk-Othmer, *Encyclopedia of Chemical Technology*, Fourth Ed., Wiley-Interscience, NY, vol. 15, pp. 159-177, 1995, which is incorporated herein by reference.

In another embodiment, the present invention provides novel processes for making leather by harvesting skin from livestock which have been fed such a feedstuff and converting the skin into leather. In the context of the present invention, the term leather also includes suede and the term skin include hides and pelts. The livestock in this embodiment are those whose skin may be converted into leather, such as cattle, oxen, bison, deer, pigs, goats, sheep, lambs, rabbits, lama, alpaca, foxes, mink, ermine, weasel, stoat, kangaroos, yaks, chinchilla, ostrich, emu, alligators, crocodiles, lizards, snakes, etc. The feeding may be carried out as described above in connection with the process for raising livestock. The skin may be harvested and converted into leather by conventional techniques known to those skill in the art and as described in Kirk-Othmer, *Encyclopedia of Chemical Technology*, Fourth Ed., Wiley-Interscience, NY, vol. 15, pp. 159-177, 1995, which is incorporated herein by reference.

The present invention is directed to processes for making pet food (e.g., feed for domesticated animals, such as dogs, cats, birds, etc.). Amino acid metal chelates may be particularly useful in providing mineral content to pet food. In various exemplary embodiments, processes for making a pet food may include producing amino acid metal chelates by the methods described above, and incorporating the amino acid metal chelates into a feedstuff composition. The present invention is further directed to pet foods obtained by such processes.

Other features of the invention will become apparent from the following Examples, which are provided for the purposes of illustration of the invention and are not intended to be limiting.

EXAMPLES

Example 1

Killed bacterial cells are obtained by microfiltration of spent media used to produce lysine (lysine cell cream). The effectiveness of the lysine cell cream for use in enzyme hydrolysis is evaluated. In a first trial, a rate of hydrolysis of the lysine cell cream using swine pancreatin is evaluated by measuring Michaelis-Menten enzyme kinetics.

A pH of the lysine cell cream is adjusted to 7. The lysine cell cream is added to 50 ml round bottom polypropylene centrifuge tubes to provide six replicates of tubes including 0, 0.8, 1.6, 3.2 and 6.4 mg of nitrogen. The volume of material in each tube is made equal by adding de-ionized water. 5 mg of pancreatin (Sigma P-7545) are added to each tube. The tubes are stoppered and placed into a warm water bath (30° C.) for two hours. After two hours, enzyme activity and hydrolysis in the tubes is stopped by adding trichloroacetic acid in an amount equal to 20% of the volume in each tube.

Trichloroacetic acid precipitates proteins and peptides larger than about 3 amino acids. Subsequent to precipitation with trichloroacetic acid, any soluble nitrogen remaining in the tubes should be attributable to free amino acids, dipeptides or tripeptides.

The tubes are allowed to stand for 30 minutes after addition of trichloroacetic acid. The tubes are then centrifuged at 3,200×g for 10 minutes. The supernatant is recovered and analyzed for soluble nitrogen as kjeldahl nitrogen.

The Michaeli-Menten equation describes the relationship between the rate of substrate conversion by an enzyme (hydrolysis) to the concentration of the substrate. Velocity is the rate of conversion and $V_{max}$ is the maximum rate of conversion. The Michaelis constant, $K_m$, is equivalent to the substrate concentration at which the rate of conversion is half of $V_{max}$. The $K_m$ approximates the affinity of the enzyme for the substrate. A small $K_m$ indicates high affinity. The Michaelis-Menten equation is plotted with the change in velocity as the y-axis and the change in substrate concentration as the x-axis.

The measured nitrogen amounts and the calculated velocities for the respective samples are set forth in TABLE 1 below.

TABLE 1

| | | | | | |
|---|---|---|---|---|---|
| Initial Measured N (mg) | 0 | .818 | 1.636 | 3.272 | 6.545 |
| Measured Soluble N After Precipitation (mg) | 0.0153 | 0.5955 | 1.1166 | 2.0310 | 3.1546 |
| Velocity (mg soluble N/hr/mg enzyme) | 0.0015 | 0.0595 | 0.1117 | 0.2031 | 0.3155 |

Figure 1:
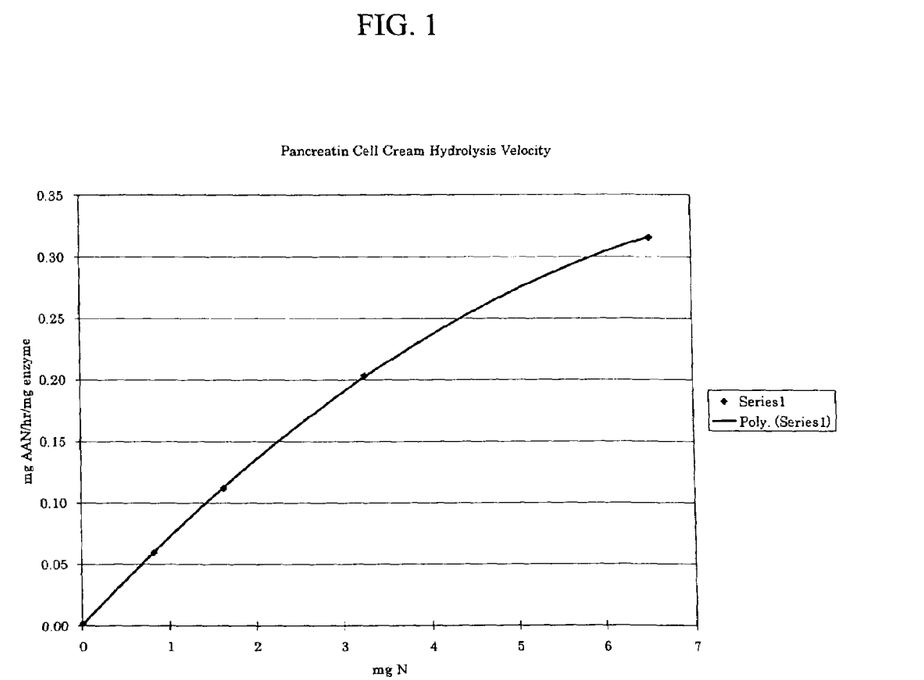
FIG. 1 is a graph showing a relationship between change in velocity and change in substrate concentration in exemplary hydrolysis reactions according to the present invention.
Figure 2:
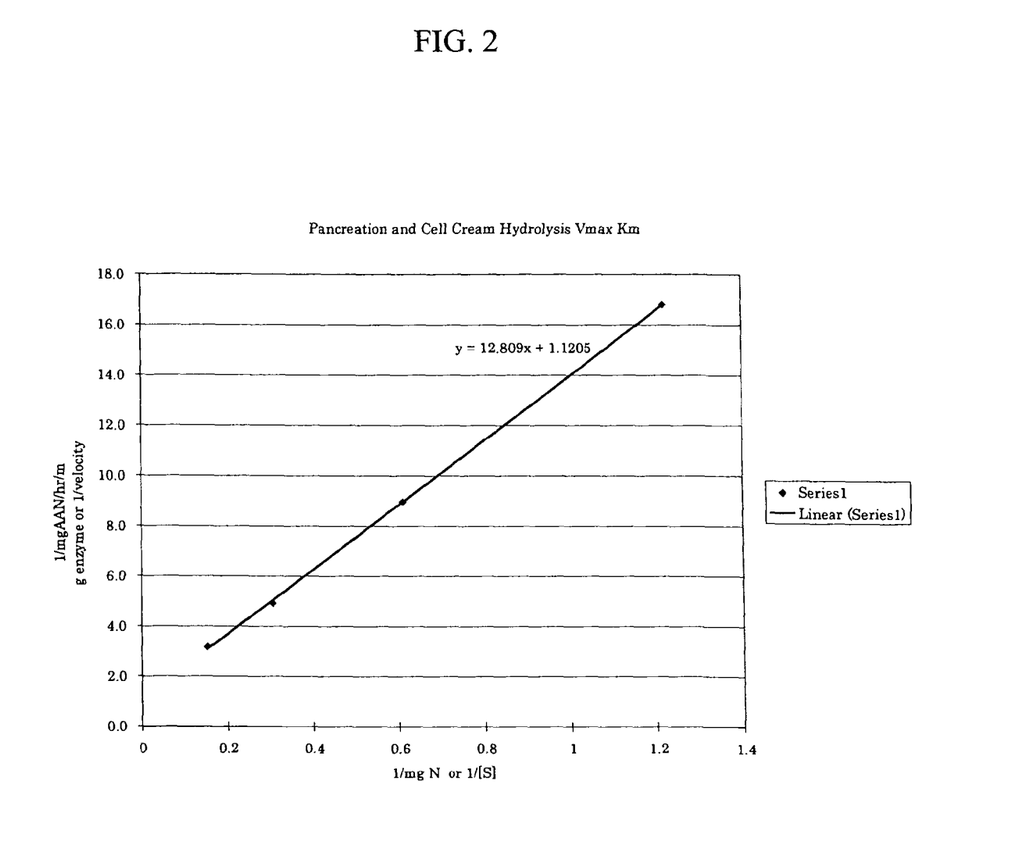
FIG. 2 is a graph showing a relationship between an inverse of change in velocity and an inverse in change in substrate concentration in exemplary hydrolysis reactions according to the present invention.

As is evident from the data in TABLE 1, as substrate concentration increases, the velocity of hydrolysis increases. The Michaelis-Menten curve derived from the data in TABLE 1 is plotted in FIG. 1. The inverse of the data plotted in FIG. 1 (Lineweaver-Burk equation) is plotted in FIG. 2—the inverse of change in velocity as the y-axis and the inverse of the change in substrate concentration as the x-axis. The plot in FIG. 2 is a straight line that can be used to calculate $K_m$ and $V_{max}$ for the obtained data. The y-intercept of the line in FIG. 2 is the inverse of $V_{max}$ and the slope of the line is $K_m/V_{max}$. From the equation of the line in FIG. 2, $V_{max}$ is calculated to be 0.8924 mg soluble N/hr/mg of enzyme. Accordingly, one kilogram of bacterial protein nitrogen (bacterial cells have approximately 12.5% nitrogen content) hydrolyzed for 48 hours would be expected to require 23.35 g of pancreatin or 2.34 enzyme/nitrogen weight percent, in theory. The same amount of protein nitrogen hydrolyzed for only 18 hours would be expected to require 62.25 g of enzyme or 6.23 enzyme/nitrogen weight percent.

Example 2

Killed bacterial cells are obtained by microfiltration of spent media used to produce lysine (lysine cell cream). The effectiveness of pancreatin for use in hydrolyzing the lysine cell cream is evaluated under differing moisture conditions.

Nine samples are prepared, each including lysine cell cream, pancreatin and de-ionized water, with the exception of a control, which does not include any enzyme or water. The non-control examples include lysine cell cream and pancreatin in the same ratio (2.2 g pancreatin/100 g protein nitrogen), but include differing amounts of water. A pH of each of the non-control examples is adjusted to 9.0. Each of the samples is provided in a 500 ml baffled Erlenmeyer flask and placed onto a shaker (37° C., 120 rpm) for 18 hours. After 18 hours, each sample is treated with trichloroacetic acid to precipitate any protein or peptides larger than 3 amino acids. The samples are allowed to stand for 30 minutes after addition of trichloroacetic acid. The samples are then centrifuged at 3,200×g for 15 minutes. The supernatant is recovered and analyzed for soluble nitrogen as kjeldahl nitrogen. The percentage of protein nitrogen hydrolyzed is calculated as the amount of soluble nitrogen in the supernatant divided by the insoluble nitrogen (total nitrogen minus soluble nitrogen without enzyme added). The results are set forth in TABLE 2 below.

TABLE 2

| Example | Pancreatin (mg) | Lysine cell cream (g) | Water (g) | pH before hydrolysis | Protein N (g) | Soluble N (g/100 g) | Soluble N/insoluble N (g/100 g) |
|---|---|---|---|---|---|---|---|
| Control | 0 | 302.95 | 0 | 4.00 | 3.39 | 0.22 | 0 |
| 2 | 72.00 | 293.41 | 3.83 | 8.93 | 3.29 | 0.99 | 86.61 |
| 3 | 79.00 | 300.89 | 6.24 | 9.06 | 3.37 | 1.06 | 93.86 |
| 4 | 61.08 | 249.37 | 49.63 | 8.98 | 2.79 | 1.01 | 88.23 |
| 5 | 66.79 | 252.69 | 54.27 | 9.01 | 2.83 | 1.03 | 90.51 |
| 6 | 51.55 | 199.89 | 103.43 | 9.08 | 2.24 | 1.04 | 91.36 |
| 7 | 48.56 | 202.43 | 97.43 | 9.05 | 2.27 | 1.04 | 91.45 |
| 8 | 37.14 | 151.89 | 151.59 | 9.16 | 1.70 | 1.10 | 98.27 |
| 9 | 36.80 | 149.63 | 150.23 | 9.04 | 1.68 | 1.10 | 97.21 |

As is evident from the results, there may be an advantage to lowering the total solids content of cell cream before hydrolysis. Although the enzyme to substrate ratio is constant across all treatments, the cell cream without dilution is very viscous and physical contact between enzyme and substrate may be reduced. These data show that nearly 100% of the protein nitrogen can be hydrolyzed under the most ideal conditions. These data also indicate that enzymatic hydrolysis can be even more efficient that reflected in the enzyme kinetic data obtained in Example 1. Using the value for $V_{max}$ obtained in Example 1 (0.8924 mg N/hr/mg enzyme), it can be calculated that samples 8 and 9 would require approximately 105 mg of enzyme (6.23%) to completely hydrolyze within 18 hours. However, only approximately 37 mg are added and almost 100% hydrolysis is achieved. The amount of enzyme added in the samples shown is intentionally lower than thought to be required so that treatment differences can be detected—excess enzyme can mask any effect differing conditions have on the rate of hydrolysis.

Example 3

1767 lbs of lysine cell cream (20% total solids, 16% crude protein as is) and 1 lb of pancreatin are reacted under conditions, as described above, to hydrolyze the bacterial proteins. 232 lbs of zinc sulfate are blended into the hydrolyzed bacterial proteins and reacted for a period to last between 30 minutes and 1 hour to obtain one short ton of chelated hydrolyzate solution with a solids content of no more than 29%. The chelated hydrolyzate solution is then dried.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of producing amino acid metal chelates, comprising:
    producing an amino acid ligand by enzymatically hydrolyzing bacterial cells; and
    reacting the amino acid ligand with a metal cation;
    wherein:
    the bacterial cells are obtained as a by-product of amino acid production; and
    the bacterial cells are provided in spent media from production of at least one amino acid selected from the group consisting of arginine, histidine, isoleucine, leucine, lysine, methionine, phenylalanine, threonine, tryptophan, valine, glycine, serine, cysteine, tyrosine, alanine, aspartic acid, glutamic acid, proline, asparagine, and glutamine.

2. The method of claim 1, wherein producing amino acid metal chelates comprises producing metal chelates of at least one of free amino acids, dipeptides and tripeptides.

3. The method of claim 1, wherein enzymatically hydrolyzing bacterial cells comprises hydrolyzing a cell cream having a solids content of from about 1 to about 30 weight percent.

4. The method of claim 1, wherein enzymatically hydrolyzing bacterial cells comprises hydrolyzing a cell cream having a nitrogen content of from about 0.12 to about 4 weight percent.

5. The method of claim 1, wherein enzymatically hydrolyzing bacterial cells comprises hydrolyzing with at least one enzyme that is capable of hydrolyzing bacterial proteins into at least one of free amino acids and short peptides.

6. The method of claim 1, wherein enzymatically hydrolyzing bacterial cells comprises hydrolyzing with a mixture of one or more enzymes of plant origin, enzymes of animal origin, enzymes of bacterial origin and enzymes of fungal origin.

7. The method of claim 1, wherein enzymatically hydrolyzing bacterial cells comprises hydrolyzing with at least one member selected from the group consisting of proteases, lipases and amylases.

8. The method of claim 1, wherein enzymatically hydrolyzing bacterial cells comprises hydrolyzing with at least one member selected from the group consisting of pancreatin, papain, bromelain, bacterial protease, fungal protease, trypsin, chymotrypsin, pepsin and rennin.

9. The method of claim 1, wherein producing an amino acid ligand by enzymatically hydrolyzing bacterial cells comprises combining an enzyme and the bacterial cells in a weight ratio of from about 0.1 to about 10 g of enzyme per 100 g of nitrogen content of bacterial cells.

10. The method of claim 1, wherein producing an amino acid ligand by enzymatically hydrolyzing bacterial cells comprises reacting an enzyme and the bacterial cells in the presence of a catalyst.

11. The method of claim 10, wherein the catalyst comprises at least one member selected from the group consisting of iron, copper, cobalt, nickel, boron, magnesium, calcium and rare earth metals.

12. The method of claim 1, wherein reacting the amino acid ligand with a metal cation comprises reacting the amino acid ligand with a metal cation having a valence of two or more.

13. The method of claim 1, wherein reacting the amino acid ligand with a metal cation comprises reacting the amino acid ligand with at least one metal cation selected from the group consisting of calcium, magnesium, chromium, manganese, iron, copper, cobalt, boron, molybdenum, vanadium and zinc.

14. The method of claim 1, wherein reacting the amino acid ligand with a metal cation comprises reacting the amino acid ligand with a salt of the metal cation.

15. A method of producing amino acid metal chelates, comprising:
producing an amino acid ligand by enzymatically hydrolyzing bacterial cells; and
reacting the amino acid ligand with a metal cation;
wherein enzymatically hydrolyzing bacterial cells comprises hydrolyzing with at least one enzyme that is capable of hydrolyzing bacterial proteins into at least one of free amino acids and short peptides.

16. The method of claim 15, wherein producing amino acid metal chelates comprises producing metal chelates of at least one of free amino acids, dipeptides and tripeptides.

17. The method of claim 15, wherein the bacterial cells are obtained as a by-product of an industrial process that generates bacterial mass.

18. The method of claim 17, wherein the industrial process is selected from the group consisting of ethanol production, organic acid production, and waste-water treatment.

19. The method of claim 15, wherein the bacterial cells are obtained as a by-product of amino acid production.

20. The method of claim 19, wherein the bacterial cells are provided in spent media from production of at least one amino acid selected from the group consisting of lysine, threonine, tryptophan and glutamic acid.

21. The method of claim 15, wherein enzymatically hydrolyzing bacterial cells comprises hydrolyzing a cell cream having a solids content of from about 1 to about 30 weight percent.

22. The method of claim 15, wherein enzymatically hydrolyzing bacterial cells comprises hydrolyzing a cell cream having a nitrogen content of from about 0.12 to about 4 weight percent.

23. The method of claim 15, wherein enzymatically hydrolyzing bacterial cells comprises hydrolyzing with a mixture of one or more enzymes of plant origin, enzymes of animal origin, enzymes of bacterial origin and enzymes of fungal origin.

24. The method of claim 15, wherein enzymatically hydrolyzing bacterial cells comprises hydrolyzing with at least one member selected from the group consisting of proteases, lipases and amylases.

25. The method of claim 15, wherein enzymatically hydrolyzing bacterial cells comprises hydrolyzing with at least one member selected from the group consisting of pancreatin, papain, bromelain, bacterial protease, fungal protease, trypsin, chymotrypsin, pepsin and rennin.

26. The method of claim 15, wherein producing an amino acid ligand by enzymatically hydrolyzing bacterial cells comprises combining an enzyme and the bacterial cells in a weight ratio of from about 0.1 to about 10 g of enzyme per 100 g of nitrogen content of bacterial cells.

27. The method of claim 15, wherein producing an amino acid ligand by enzymatically hydrolyzing bacterial cells comprises reacting an enzyme and the bacterial cells in the presence of a catalyst.

28. The method of claim 27, wherein the catalyst comprises at least one member selected from the group consisting of iron, copper, cobalt, nickel, boron, magnesium, calcium and rare earth metals.

29. The method of claim 15, wherein reacting the amino acid ligand with a metal cation comprises reacting the amino acid ligand with a metal cation having a valence of two or more.

30. The method of claim 15, wherein reacting the amino acid ligand with a metal cation comprises reacting the amino acid ligand with at least one metal cation selected from the group consisting of calcium, magnesium, chromium, manganese, iron, copper, cobalt, boron, molybdenum, vanadium and zinc.

31. The method of claim 15, wherein reacting the amino acid ligand with a metal cation comprises reacting the amino acid ligand with a salt of the metal cation.

* * * * *